United States Patent [19]

del Valle et al.

[11] Patent Number: 5,158,751
[45] Date of Patent: Oct. 27, 1992

[54] LIQUID METERING AND TRANSFER VALVE ASSEMBLY

[75] Inventors: Roberto del Valle; Santos E. Vargas; Pedro P. Cabrera, all of Miami, Fla.

[73] Assignee: Coulter Corporation, Hialeah, Fla.

[21] Appl. No.: 626,936

[22] Filed: Dec. 13, 1990

[51] Int. Cl.$^5$ .................................................. G01N 1/20
[52] U.S. Cl. ............................... 422/103; 73/863.73; 73/864.12; 251/355
[58] Field of Search .......................... 422/103, 100; 73/863.73, 864.12, 864.84, 864.21; 251/355

[56] References Cited

U.S. PATENT DOCUMENTS

| | | | |
|---|---|---|---|
| 2,656,508 | 10/1953 | Coulter | 73/861.04 |
| 3,567,390 | 3/1971 | Rothermel | 422/103 |
| 3,966,439 | 6/1976 | Vennos | 73/863.23 |
| 4,152,391 | 5/1979 | Cabrera | 422/103 |
| 4,387,076 | 6/1983 | Cabrera et al. | 422/65 |
| 4,445,391 | 5/1984 | Cabrera | 422/103 |
| 4,507,977 | 4/1985 | Cabrera | 422/103 |
| 4,577,515 | 3/1986 | Someya et al. | 73/863.73 |
| 4,702,889 | 10/1987 | Cabrera et al. | 422/103 |
| 4,726,932 | 2/1988 | Feier et al. | 422/103 |
| 4,822,569 | 4/1989 | Pelligrino | 73/863.73 |
| 4,896,546 | 1/1990 | Cabrera et al. | 73/863.73 |
| 4,948,565 | 8/1990 | Bemis et al. | 422/103 |
| 4,957,008 | 9/1990 | Proni et al. | 73/863.73 |

Primary Examiner—Lynn M. Kummert
Attorney, Agent, or Firm—Sidney N. Fox; Gerald R. Hibnick

[57] ABSTRACT

A liquid metering and transfer valve assembly having the capability of metering, isolating, transfering and delivering precise microliter volume aliquots of a blood sample, from a source thereof, to mixing and testing chambers of an electronic blood analysis system for analysis, and further, carrying a loop for metering and isolating an additional sample aliquot within the valve assembly in the loop, a first dedicated passageway for introducing a first fluid to the loop to force the additional aliquot from its isolated location to a first dedicated portion of the valve assembly displaced from the loop and a second dedicated portion of the valve assembly to establish a flow path for introducing a lysing reagent to the first dedicated portion to force the additional aliquot from its displaced disposition, as a lyse reagent/aliquot mixture, to a selected additional mixing and testing chamber exterior of the valve assembly without contaminating any interior flow path traversed by a blood sample and associated diluent thereof within the valve assembly.

15 Claims, 5 Drawing Sheets

FIG. 7B

LIQUID METERING AND TRANSFER VALVE ASSEMBLY

This invention relates generally to metering and transfer valve assemblies for use in blood analysis systems of the type having the capability of metering, isolating, transferring and delivering precise microliter volume aliquots of a whole blood sample from a single source thereof, to mixing and testing means of said system located exterior of the valve assembly.

More particularly, the invention provides a three disc rotary metering and transfer valve assembly having the capability of metering and isolating precise volume aliquots of the blood sample from a single source thereof for providing dilutions, and, in addition, having means as a part thereof, to drive at least one sample aliquot to a location displaced from its internal measuring location and having means to introduce a lysing reagent to said aliquot at that displaced location for delivery of the sample aliquot/lysing reagent mixture to a select mixing and testing chamber exterior of the valve assembly, whereby a lysed blood sample is delivered via the same valve assembly that handles the provision of blood sample aliquots for providing dilutions and without contaminating any interior flow paths within the valve assembly and their associated diluent flow paths.

Reference has been made to U.S. Pat. Nos. 2,656,508, 3,549,994 and others. The valve assemblies to which reference has been made preferably comprise a pair of stationary valve disc elements sandwiching a center, rotatable valve disc element, said elements arranged coaxially with the faces of the center element frictionally sealingly engaged with the adjacent faces of the stationary elements. These valve assemblies have achieved considerable commercial success and have included internal passageway means of precise interior volume to provide precise volumes of liquid sample for dilution. Preferably, a series flow path was defined through the valve assembly for the receipt of a continuous body of blood sample from a source thereof. This series flow path included segmenting passageway means and segmenting portions, each having a precise interior volume. Upon rotation of the center valve element, the loaded series flow path was segmented to define the precise volume aliquot portions which were individually isolated. Predetermined volumes of diluent were introduced to each of the aliquot portions driving respective ones with associated diluent to mixing and testing vessels exterior of the valve assembly for the determination of various parameters of the blood sample. The determination of certain of said parameters requires the lysing of the dilution with lysing reagent. It would also be advantageous to measure the aliquot of blood sample which is to be lysed simultaneously with the measurement of the other blood sample aliquots so that all would constitute the same batch and would thus be better correlated. Further, it would be most advantageous to effect the drawing of all three sample portions in a single step. This would be most efficiently effected by employing a single metering and transfer valve. Heretofore this has not been possible since the lysing reagent has corrosive properties and, of course, would contaminate those interior portions of the valve assembly which carry the blood samples or which may contact either the diluent or blood flow paths within the valve assembly, and hence contaminate those samples and/or dilutions which must not be exposed to the lysing reagent. Even traces of lysing reagent would deleteriously effect the other liquids traversing the interior of the valve assembly.

Accordingly, the exposure of the valve assembly interior to or the presence of any lysing reagent within the valve assembly used to provide dilutions has to be avoided. Thus, addition of such reagent conventionally occurs outside the valve assembly along individual dedicated lines and flow paths leading from a source of lysing reagent to the specific mixing and testing vessel containing the blood sample dilution which must be treated therewith. This has required a separate valve assembly additional to the blood metering and transfer valve.

It has become desirous to determine certain characteristics of whole blood by means other than apparatus based directly upon the Coulter principle yet provide for such determinations via the same instrument operating under the Coulter principle. This may require lysing of an undiluted whole blood sample with lysing reagent. To accomplish such task, a second or additional blood sampling and transfer valve assembly was required to be dedicated to the task of metering a blood sample aliquot and, either directly or indirectly handling the lysing reagent through that valve assembly or to direct the measured blood sample undiluted to a location where lysing reagent can be mixed therewith. With a separate blood sampling and transfer valve, all the blood characteristics determined would not arise from the same sample. If the lyse reagent was handled within the valve assembly, a residual trace or greater of lysing reagent remained therewithin and great care and effort was required to remove such trace by multiple rinsing with detergents and diluent. If one attempted to direct lysing reagent through the same valve assembly used to provide the dilutions as used to provide the non-diluted volume for lysing, the poisoning of the interior flow paths with lysing reagent was unavoidable under the available valve assembly constructions. Further, conservation of the available blood sample is a problem because such sample quantities were limited. As implied above, it also is important that all the determinations of the blood characteristics of a sample be determined from a sample taken from the same source batch, preferably at the same time.

SUMMARY OF THE INVENTION

The invention provides, in a liquid sampling and transfer valve assembly of the type capable of measuring and delivering plural precise volumes of whole blood sample aliquots as dilutions to mixing and testing chambers exterior of the valve assembly, means for introducing lysing reagent to one of said whole blood aliquots and delivering same as a undiluted mixture to an additional mixing and testing chamber without any contamination of any interior portions thereof within which whole blood samples and associated fluids come into contact.

DESCRIPTION OF PREFERRED EMBODIMENTS

The referenced patents provided a rotary three-disc whole blood metering and transfer valve assembly capable of metering blood sample aliquot volumes or portions and combining each of the sample aliquots with predetermined volumes of diluent for forming and delivering precise dilutions of said sample aliquots to exterior mixing and testing chambers. In addition to the dilutions, the invention provides means for metering and isolating an additional (selected) sample aliquot volume from the same sample source simultaneously with the other sample aliquots and delivering said selected sample aliquot volume with a volume of lysing reagent to an additional mixing and testing chamber, say for determination of a 5-part differential analysis of the said blood sample. Fluid, such as air or other inert gaseous fluid, is employed to position the selected aliquot sample volume at a location displaced from the rotor element of the valve assembly and the lysing reagent being passed through the valve assembly along a dedicated path therefor therewithin flushing both said sample aliquot and lysing reagent to said additional mixing and testing chamber whereby the flow paths within said valve assembly traversed by the whole blood sample and the diluent associated therewith are maintained free of contamination by the lysing reagent.

Referring to the drawings, the valve assembly according to the invention is designated generally in the FIGS. by reference character 10 and comprises an outer rotatable element hereinafter referred to as the loading element 12 (illustrated in FIGS. 1A through 1C), an outer stationary element, hereinafter referred to as the stator 14 (illustrated in FIGS. 2A through 2C and the center, rotatable element, hereinafter referred to as the rotor 16 (illustrated in FIGS. 3A through 3C). The loading element 12, the stator 14 and the rotor 16 each have an axial mounting passage 18 and are mounted coaxially on a spindle 20 with their facing surfaces frictionally sealingly engaged. The elements having the same diameter with the outer elements 12 and 14 being of the same thickness and the center element 16 being thinner than elements 12 and 14.

Figure 1A:
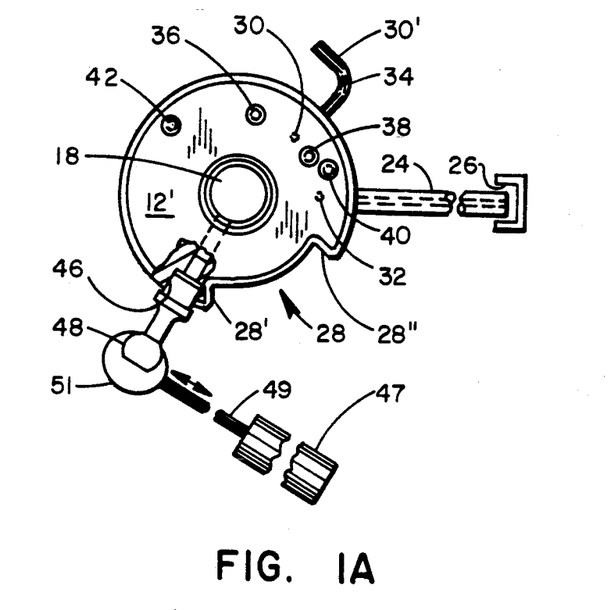
FIGS. 1A and 1B are plan views of the outer rotor element of the valve assembly according to the invention.
Figure 1B:
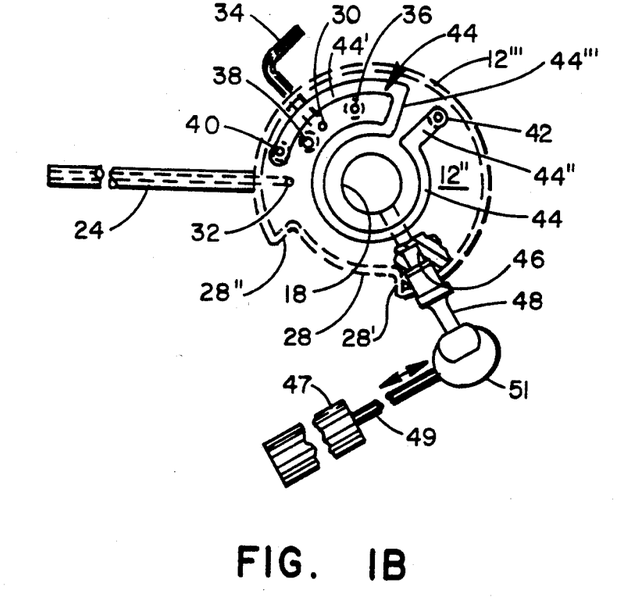
Figure 1C:
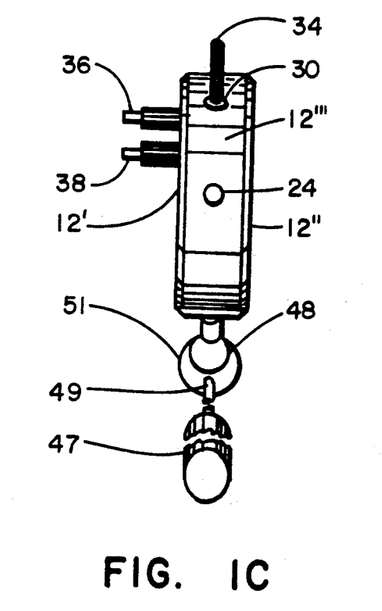
FIG. 1C is a fragmentary top view of the outer rotor element illustrated in FIGS. 1A and 1B.

The loading element 12 is translatable between two angular positions, the first being adapted to enable reception of the whole blood sample via piercing needle means 22 such as described in U.S. Pat. No. 4,387,076 in a mode described as an automatic aspiration mode. The loading element is adapted, when placed in the second angular position, to enable reception of the whole blood sample via aspirator probe 24 secured thereto, in what shall be termed a manual aspiration mode. The loading element 12 is provided with an arcuate circumferential notch 28 opening to the outer circumferential surface 12''' and having opposite walls 28' and 28'' functioning to define the rotational limits between the automatic and manual aspiration positions.

The loading element 12 is provided with a pair of spaced angular sample inlet passageways 30 and 32 opening at their outer ends to the circumferential surface 12''' of loading element 12 while opening at their inner ends to the inner facing surface 12''. Both angular passageways 30 and 32 have radial portions 30' and 32' and inner, axially parallel portions 30'' and 32'' which open to said surface 12''. Suitable elbow 34 is seated securely within the radial portion 30' to provide for coupling to the piercing needle means 22 and the aspiration probe 24 is seated securedly within the radial portion 32'. Through axially parallel passageways 36 and 38 are formed in the loading element 12 spaced the same center to center distances from the axially parallel portions 30'' and 32'' of said angular passageways 30 and 32 respectively, the center axes of said passageways 36 and 38 and the axially parallel portions 30'' and 32'' intersecting a circular line concentric with the axial passage 18. The loading element 12 also carries axially parallel passageways 40 and 42.

Axially parallel through passageways 36 and 38, which can be described as complementary cooperating counterpart passageways, cooperate with angular passageways 30 and 32 respectively to direct diluent to the whole blood sample aliquot volume subsequent to isolation thereof (when the valve assembly has been placed in the segmentation or isolation [delivery] mode). Axially parallel passageways 40 and 42 open to the catch channel means 44 formed in the inner surface 12'' of the loading element and serve as the inlet and outlet respectively for rinse liquid functioning to flush the catch channel means 44 of any material which may have accumulated therein after escaping from the junctions of any interior passageways, said junctions being located at the frictionally engaged surfaces of said loading element 12 and the rotor 16 and which may have travelled along said surfaces toward the inner and/or the outer circumference of said valve assembly 10, say by capillarity.

The loading element 12 also is provided with a radially directed socket 46 opening to the outer circumferential surface 12'''. A stud 48 is seated securely within said socket 46 and extends outward thereof terminating with a ball-like formation 48'. A fluid activated cylinder 47 can be provided exterior of the valve assembly 10 for reciprocably operating piston rod 49. The free end of piston rod 49 can be coupled to the member 51 which is provided with a recess 53 conforming to the formation 48'. Formation 48' is secured to member 51 and receives said formation 48'. Thus the operation of the piston rod 51 enables the loading element 12 to be selectively rotated mechanically to select either the automatic or the manual aspiration or loading modes, the angular rotation required to reach one or the other of said modes being 45 degrees.

The loading element 12 is illustrated in FIG. 1A viewing the outer surface 12′ while in FIG. 1B, the loading element 12 is illustrated with the surface 12″ facing the viewer. As shown in FIG. 1B, the first catch-channel means 44 is formed in the surface 12″ of the said loading element 12 and comprises an outer, arcuate portion 44′ into which passageway 40 opens, an inner generally circular portion 44″ (which extends substantially surrounding the axial passage 18), a linking portion 44″″ joining portions 44′ and 44″ and a radially directed portion 44‴ into which the passageway 42 opens.

Figure 2A:
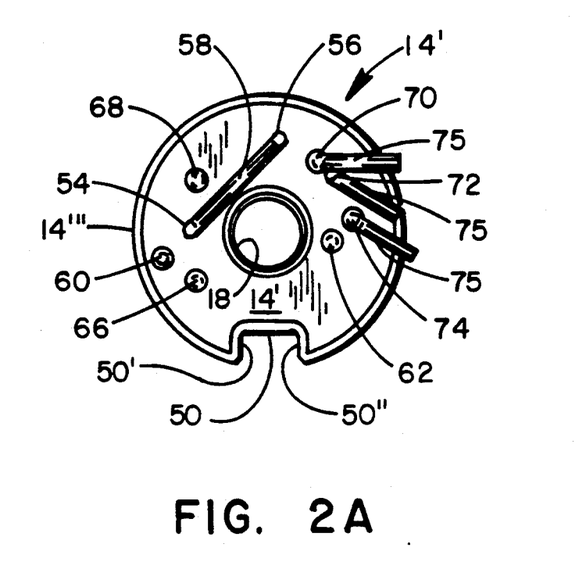
FIGS. 2A and 2B are plan views of the stator element of the valve assembly according to the invention.
Figure 2B:
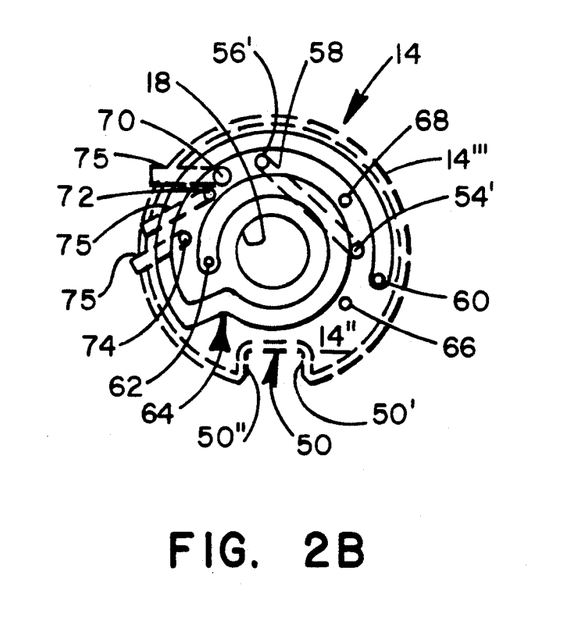
Figure 2C:
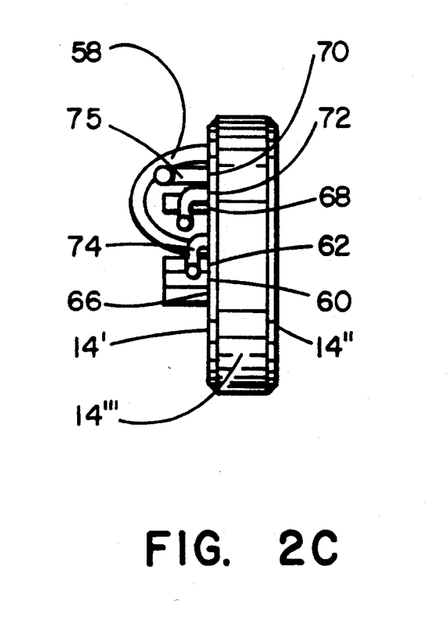
FIG. 2C is a side elevational view of the stator element illustrated in FIGS. 2A and 2B.

The stator element 14 of valve assembly 10 is illustrated in FIGS. 2A through 2C, the outer surface 14′ facing the viewer in FIG. 2A and the inner surface 14″ facing the viewer in FIG. 2B. The stator 14 is provided with a pair of opposite parallel surfaces, outer surface 14′ and inner surface 14″. Stator 14 also has an outer circumferential surface 14‴ and an axial passage 18 to receive the spindle 20. The stator 14 is provided with a rectangular configured circumferential notch 50 having opposite walls 50′ and 50″ and opening to the outer circumferential surface 14‴, the notch 15 functioning so cooperate with means (not shown) to immobilize the stator 14 and prevent its angular movement.

Axially parallel through passageways 54 and 56 are formed in the stator 14. A first hollow loop 58 is seated sealingly securely within the openings 54′ and 56′ of passageways 54 and 56 to the surface 14′ of said stator 14 so that the loop 58 extends outward of said outer surface 14′. The first hollow loop 58 has a precise interior volume suitable to define an aliquot volume of whole blood sample employed for the WBC determination as diluted with a predetermined volume of diluent.

The sensor 14 carries axially parallel through passageways 60 and 62 formed therein. Second catch-channel means 64 is formed in the inner surface 14″ with the axially parallel passageways 60 and 62 opening thereinto, passageway 60 defining the entry for rinse liquid and passageway 62 defining the outlet for rinse liquid flushing the second catch-channel means 64 of any accumulated material which may have been intercepted within the second catch-channel means 64 after escaping from the junctions of any of the internal passageways at the facing surfaces 14″ and 16″ (of the rotor 16). The stator 14 also is provided with axially parallel through passageways 66, 68, 70, 72 and 74. Passageway 66 functions as the outlet for whole blood sample during the loading mode of the valve assembly 10 and functions as the inlet for feeding rinse liquid (backwash) to the flow path of said whole blood sample while the valve assembly 10 is in the returned or backwash mode. Passageway 68 functions as a dedicated passageway through which lysing reagent is passed during the delivery of said lysing reagent to flush a selected blood sample aliquot volume in accordance with the invention herein. The passageway 68 also functions as a portion of the flow path for the said selected whole blood sample as it is flushed from its isolated location within the valve assembly to a location displaced from said isolated location and free of the rotor by a fluid which may be a gaseous fluid such as air or an inert gas, in accordance with the invention herein, as will be described hereinafter.

Passageway 70 functions to introduce the inert fluid, such as air from an air pump, to the isolated location for the aforementioned selected whole blood sample aliquot volume for directing said aliquot volume from its isolated location to its displaced location via the dedicated passageway 68. Passageway 72 serves two functions alternatively. During the loading mode, passageway 72 is coupled to a source of vacuum as to draw the sample into the probe 24. During the backwash or rinse mode, passageway 72 is coupled to a source of rinse liquid (diluent) in the form of a pump, to force said rinse liquid (diluent) along the path traversed by the WBC aliquot volume. Passageway 74 functions as an outlet to direct the whole blood sample aliquot volume isolated within the valve assembly 10, which aliquot volume is employed for the determination of the RBC characteristics of the whole blood sample, to the RBC mixing and testing chamber 52 by the introduction of a predetermined volume of diluent to flush same to said last mentioned isolated aliquot volume and form the required dilution. Suitable elbows 75 are seated in the respective passageways' openings to the outer surface 12′ of the stator 14 to enable the couplings to be made for enabling the functions of said respective passageways to occur as described.

Figure 3A:
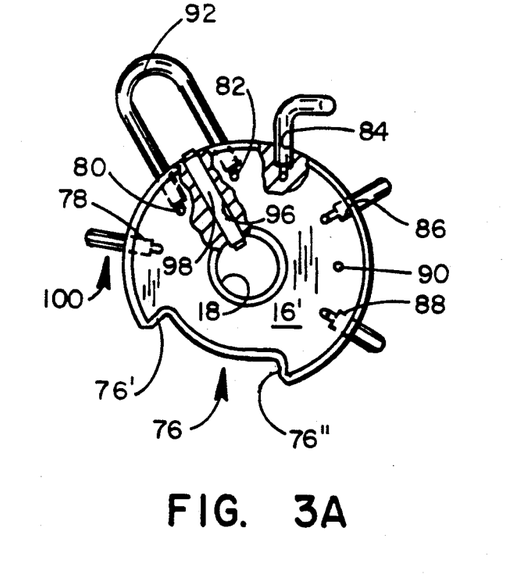
FIGS. 3A and 3B are plan views of the rotor element of the valve assembly according to the invention.
Figure 3B:
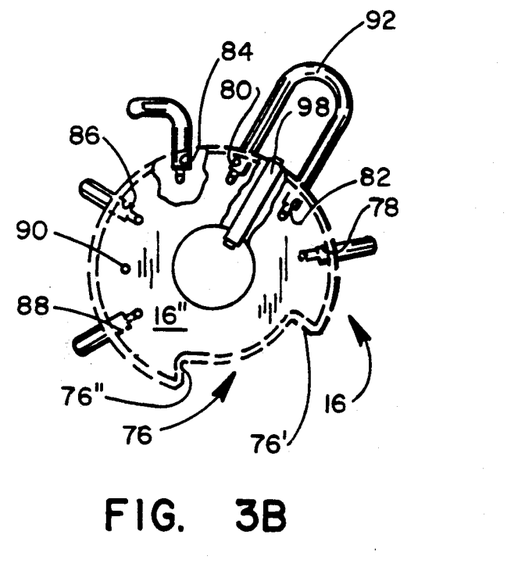
Figure 3C:
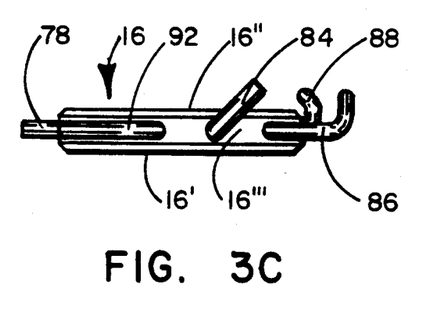
FIG. 3C is a top view of the rotor element illustrated in FIGS. 3A and 3B.

Attention now is directed to FIGS. 3A through 3C wherein the center rotatable element, rotor 16, of the valve assembly 10 is illustrated. Rotor 16 is provided with opposite parallel surfaces 16′ and 16″, along with outer circumferential surface 16‴. In FIG. 3A, the rotor 16 is illustrated with its surface 16′ facing the viewer, said surface being frictionally sealingly engaged with the surface 12″ of the loading element 12 when the valve assembly 10 is assembled in operating condition. In FIG. 3B, the rotor 16 is illustrated with its surface 16″ facing the viewer, said surface being frictionally sealingly engaged with the surface 14″ of the stator 14 when the valve assembly 10 is assembled in operating condition. The rotor 16 has the same diameter as the loading element 12 and the stator 14 and is provided with a circumferential arcuate notch 76 opening to the outer circumferential surface 16‴, said notch 76 having opposite walls 76′ and 76″ serving to limit the rotation of the rotor 16. As illustrated in FIGS. 3A and 3B, the rotor 16 is disposed in its orientation at the aspirating or loading mode of operation.

The rotor 16 is provided with six angular passageways 78, 80, 82, 84, 86 and 88, having their entry openings formed through the circumferential surface 16‴ of said rotor 16 to enter their radially inward portions to intersect with their axially parallel portions respectively opening to the surface 16″ of the rotor 16. Suitable elbows are seated within the radial portions of the respective angular passageways to permit communication with the exterior of the valve assembly 10. An axially parallel through passageway 90 is provided in rotor 16, said passageway 90 having a precise interior volume and functioning as the isolating or measuring chamber for the RBC whole blood sample aliquot volume which is isolated therein when the rotor 16 is translated to place the valve assembly 10 in the segmenting or isolating (delivery) mode of operation, as will be described hereinafter.

Passageway 78 functions as the inlet for introducing lysing reagent into the valve assembly 10 for the delivery of the aforementioned selected isolated whole blood sample aliquot, as will be described hereinafter. Passageways 80 and 82 seat the second hollow loop 92 sealing secured engaged within the radial portions thereof, said second loop 92 functioning as the measuring or isolating chamber for the selected whole blood aliquot which is to be treated with lysing reagent. Passageway 86 functions as the inlet for feeding the predetermined volume of diluent to the first hollow loop 58 for flushing the isolated content thereof to the WBC mixing and testing chamber 94 during the delivery of the WBC dilution to said chamber 94 when the valve assembly is placed in the segmentation and delivery mode of operation subsequent to the loading of the valve assembly with the whole blood sample. Passageway 84 functions to introduce rinse liquid (diluent) to the flow path of the RBC aliquot volume during the backwash of the flow path traversed by the RBC aliquot volume. Passageway 88 functions as the outlet for directing the WBC aliquot volume from the first hollow loop 58 to the WBC mixing and testing chamber 94 along with the predetermined volume of diluent introduced to the first loop 58 via the passageway 86.

The rotor 16 also is provided with radial through passageway 96 leading from the outer circumferential surface 16''' to the axial passage 18 thereof and receives pin 98 therethrough for engaging the spindle 20 to enable the rotation of said rotor 16. The axial centers of the axially parallel portions of said angular passageways 78, 80, 82, 84, 86 and 88, as well as the axial center of passageway 90, intersect a circular line concentric with passage 18 and are spaced equally from their neighboring passageways and are likewise spaced equally from the outer circumference of said rotor 16. The passageways above which are employed to pass diluent to the isolated sample aliquot volumes may also be described as complementary cooperating counterpart passageways.

Figures 4, 5:
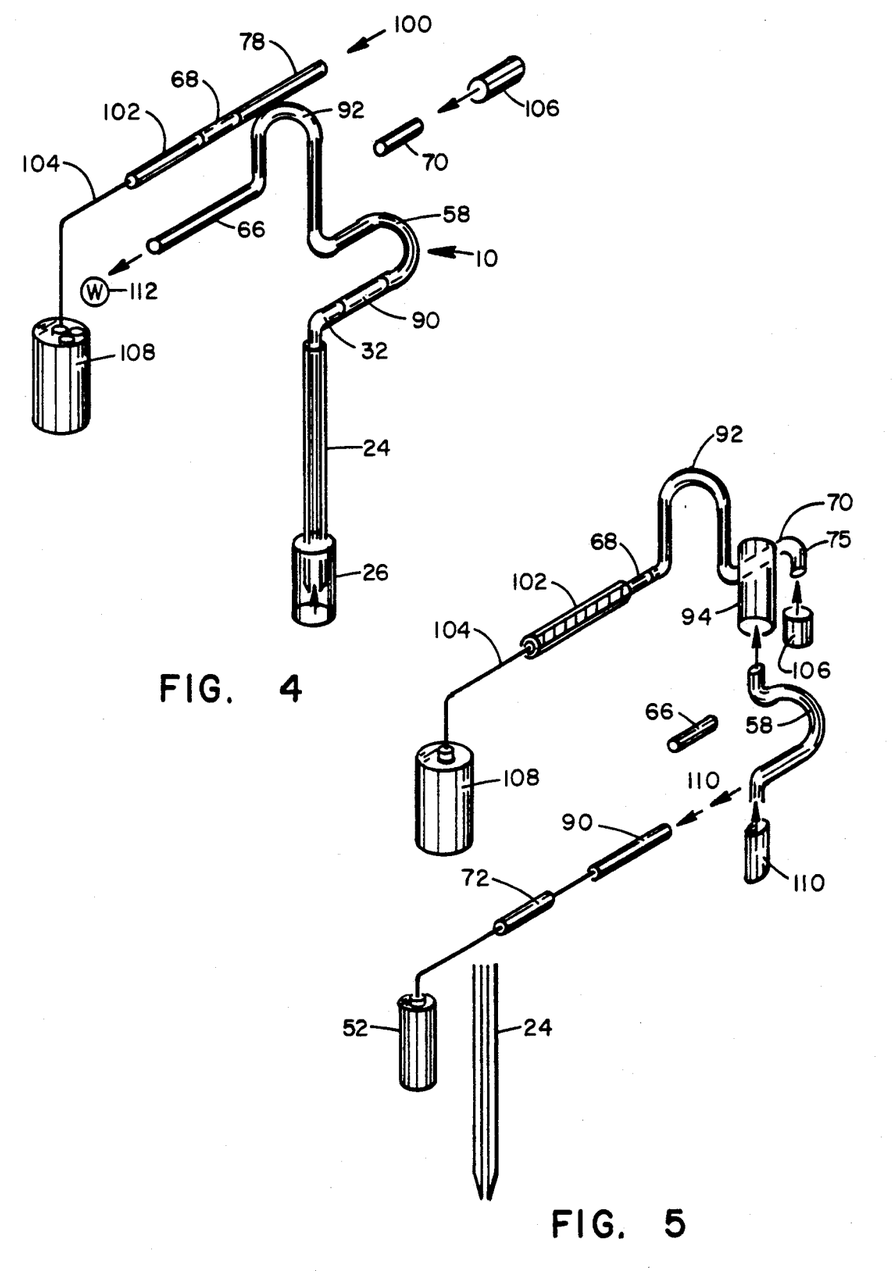
FIG. 4 is a diagrammatic representation of the valve assembly according to the invention illustrated in the loading or aspiration mode of operation.
FIG. 5 is a diagrammatic representation of the valve assembly according to the invention illustrated in the segmentation or isolation mode of operation.

The operation of the valve assembly 10 according to the invention may better be understood by reference to FIGS. 4 through 7B. In FIG. 4, a diagrammatic representation of the valve assembly 10 disposed in the aspiration or loading mode of operation is illustrated. While the loading element 12 can be rotated between a position selecting the automatic mode of operation via piercing needle means 22, the illustrated mode of loading operation selected is the manual mode where the whole blood sample is introduced to the valve assembly 10 from the single source 26 via the aspirator probe 24 by drawing a vacuum on the sample outlet port 66. In the aspiration or loading mode of operation, the RBC isolating or measuring chamber (passageway 90 in the rotor 16), the first hollow loop 58 (for the WBC aliquot volume) and the second hollow loop 92 (for the selected aliquot volume [which is to be lysed without dilution for use in the determination of the 5-part differential characteristic]) are aligned to define a continuous series flow path for the whole blood sample. The RBC aliquot measuring chamber 90 thus is carried by the rotor 16 while the WBC aliquot measuring chamber, hollow loop 58, is carried by the stator 14.

With the valve assembly 10 disposed in the loading mode of operation, the source of lysing reagent (lyse pump 100), the lysing reagent inlet 78 (in the rotor 16), the dedicated passageway 68 (in the stator 14), a storing conduit 102 and the coupling conduit 104 are series coupled, leading to the additional mixing and testing chamber 108 for performance of the 5-part differential determination, and are filled with lysing reagent from the previous last operation of the valve assembly. The second loop 92 is filled with fluid, such as air from air pump 106 or other inert gaseous fluid which was employed to flush the loop 92 of the prior loaded selected whole blood aliquot. The air pump 106 is blocked from delivering fluid to the loop 92 by the facing surface 14'' of the stator 14.

Now the rotor 16 is ready to be rotated to place the valve assembly 10 in its segmentation or isolation (delivery) mode during which the whole blood sample aliquot volumes are isolated within the aforementioned measuring chambers. Immediately prior to the rotation of the rotor 16 to the segmentation mode, the air pump 106 is activated momentarily to direct a pulse of air to the air inlet passageway 70 to assure that no whole blood sample enters said passageway during rotation of said rotor 16.

Figure 7A:
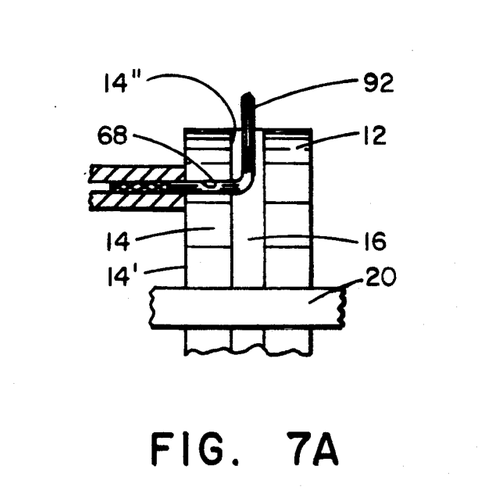

Rotation of rotor 16 is effected and the respective whole blood sample aliquots are isolated by the segmentation of the continuous body of whole blood sample in the continuous flow path defined by the serially communicating measuring chambers and sample inlet. Predetermined volumes of diluent are introduced into the valve assembly 10 via passageways 38, 54, 56 and 84 to drive the respective RBC and WBC aliquot volumes with diluent as dilutions to the respective mixing and testing chambers 52 and 108. Simultaneously, the air pump is activated to introduce air to air inlet 70, driving the selected whole blood aliquot from the hollow loop 92 to a location displaced from the rotor 16 (free of the rotor 16) and located in the storing conduit 102, air entering into the dedicated passageway 68 forcing the selected sample aliquot into the conduit 102, at least an air bubble 114 occupying the trailing end of the said selected sample aliquot volume. The position of the selected sample aliquot when same is forced from the loop 92 is represented in FIG. 7A.

Figure 6:
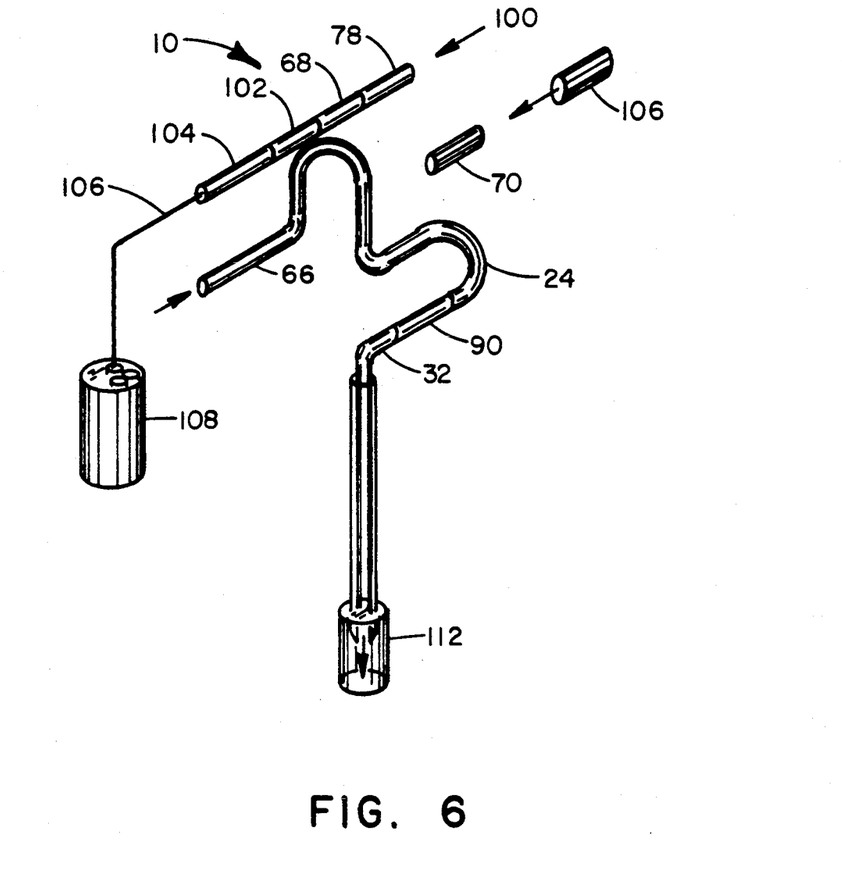
FIG. 6 is a diagrammatic representation of the valve assembly according to the invention illustrated in the completion or "backwash" mode of operation having been returned to the condition illustrated in FIG. 4 wherein there is a partial delivery of one measured sample volume and the backwash or rinsing of the portions of the valve assembly traversed by the whole blood sample and diluent associated therewith; and, FIGS. 7A and 7B are fragmentary diagrammatic sectional detail views of the valve assembly according to the invention illustrating the disposition of the selected one measured sample volume at the segmentation mode illustrated in FIG. 5 and at the completion or backwash mode illustrated in FIG. 6, respectively.

With the selected sample aliquot volume displaced from the rotor 16 and the RBC and WBC aliquot volumes directed to the respective mixing and testing chambers 52 and 94 as dilutions with the predetermined volumes of diluent, the completion of this operational mode is at hand and the rotor 16 is rotated to assume its condition during the loading mode. This can be accomplished by reverse rotation of the rotor 16.

Figure 7B:
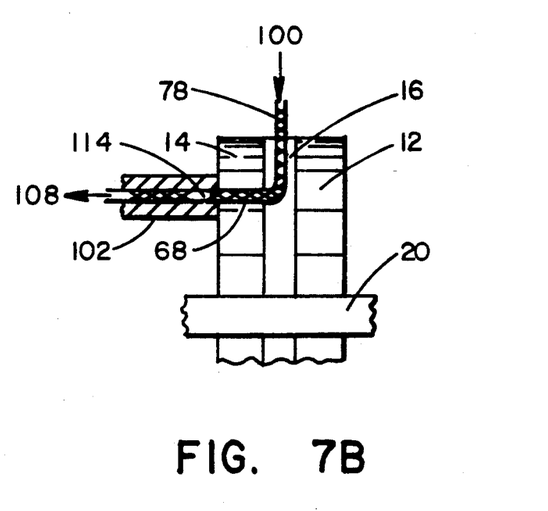

When the rotor 16 is rotated to return the valve assembly 10 to its condition during loading (FIG. 4), the lyse pump 100 is activated to introduce lysing reagent to the lysing reagent inlet passageway 78 which is aligned with the dedicated passageway 68, driving the selected blood sample aliquot (undiluted) along with said lysing reagent to said additional mixing and testing chamber 108. The flow path as existent during the aspiration or loading condition of the valve assembly 10 is returned by the reverse rotation of rotor 16 and diluent (or rinse liquid) is directed from a source 110 thereof to the passageway 66 and through the series communicating second loop 92, the first loop 58, the passageways 90 and 32 to and through the aspiration probe 24 to a waste reservoir represented by reference character 112, completing the backwash.

Thus the lysing reagent is utilized and passed through the same valve assembly which meters and delivers sample aliquot dilutions without any contamination of the flow path traversed by the whole blood sample and the diluent associated therewith. It is believed that the invention provides the first occasion permitting the same valve assembly to be utilized to provide blood sample dilutions and lysed blood sample (undiluted) for apparatus employed to study and determine the characteristics of such samples. It should be noted that other reagents can be substituted for lysing reagent if the blood aliquots, their flow path and associated flow paths for liquids associated therewith are not to be exposed to said other reagents.

It is believed apparent that considerable variations and substitutions of equivalents are capable of being made without in any way departing from the spirit and scope of the invention as defined in the appended claims. The invention is not intended to be limited to the provision of one measured sample volume for combination with lysing reagent introduced via the valve assembly nor is it believed to be limited to merely the achievement of one, two or more dilutions for delivery to respective testing chambers.

What we claim is:

1. In a liquid sampling, metering, isolating and delivery valve assembly for providing at least a pair of precise sample volumes from a single sample source, the valve assembly including a stator, a rotor and a loading element arranged coaxially for operation between a loading condition and a delivery condition, means carried by the rotor for defining a first precise volume isolating chamber, means carried by the stator for defining a second precise volume, isolating chamber, the first and second isolating chambers being in series communication during the loading condition for defining a continuous body of sample from the single sample source along a flow path defined within the valve assembly, the rotor being operable to segment the continuous sample body to form and isolate precise aliquot volumes from the continuous sample body within the first and second isolating chambers respectively, cooperating counterpart passageways formed in each of the rotor, stator and loading element for establishing interconnection of said isolating chambers and constructed and arranged for receiving and directing predetermined volumes of diluent to the isolated aliquot volumes for delivery of each respectively with a diluent associated therewith as precise dilutions to respective mixing and testing chambers exterior to the valve assembly, the first isolating chamber being an axially parallel through-passageway and the second isolating chamber being a first external hollow loop secured to the stator; the improvement comprising: means carried by the rotor defining a third precise volume isolating chamber arrangeable in series communication with the first and second isolating chambers during the loading condition of the valve assembly so as to form a continuing portion of the continuous sample body and, the operation of the rotor also isolating a third precise aliquot volume within said third isolating chamber simultaneously with the isolation of the first and second aliquot volumes within the first and second isolating chambers, an axially parallel, dedicated through-passageway formed in the stator, a dedicated lyse reagent entry passageway carried by the rotor and a gaseous fluid entry passageway carried by the stator and arranged to be placed in communication with said third isolating chamber simultaneously with the isolation of the first and second sample aliquot volumes, said gaseous fluid entry passageway arranged to receive and direct gaseous fluid to said third isolating chamber to position the third sample aliquot volume contained therein via said dedicated passageway to a neutral location displaced from the rotor when the valve assembly is placed in the delivery condition for the delivery of the first and second sample aliquot volumes to the first and second mixing and testing locations, the rotor being returnable to the loading condition from the delivery condition, said lysing reagent entry passageway being arrangeable in communication with said dedicated passageway to receive and deliver lysing reagent to and through said dedicated passagway and the neutral location when the valve assembly is returned to the loading condition, for delivering the third isolated sample aliquot volume along with the lysing reagent from the dedicated passageway and neutral location to a third mixing and testing chamber exterior to the valve assembly without contaminating with lysing reagent any interior flow path within the valve assembly which is traversed by the sample.

2. The valve assembly as claimed in claim 1 and, means for introducing rinse medium to the sample flow path for backwashing said flow path simultaneously with delivery of the lysing reagent and third sample aliquot volume to the third mixing and testing chamber.

3. The valve assembly according to claim 1 in which said third isolating chamber comprises a second external hollow loop carried by the rotor.

4. The valve assembly according to claim 1 in which the loading element carries sample inlet means arranged for coupling to the first isolating chamber during the loading condition and the cooperating counterpart passageway means carried by the loading element is capable of leading diluent to the first isolating chamber during the delivery condition of said valve assembly.

5. In a liquid rotary metering and transfer valve assembly for providing plural precise sample volumes from a single liquid sample source and delivering each of the precise sample volumes with respective predetermined volumes of diluent as dilutions to respective exterior mixing and testing chambers, the valve assembly including a pair of outer valve elements and a rotor element sandwiched therebetween in face to face frictional sealed engagement, one of the outer valve elements being a stator and the other of the outer valve elements being a loading valve element, first and second measuring portions carried by the stator and rotor and in series communication when the valve assembly is disposed in loading condition, the rotor being translatable to isolate the precise sample volumes within the first and second measuring portions when the valve assembly is disposed in the delivery condition, complementary cooperating counterpart passageway means carried by the rotor, the stator and the loading element for interconnecting the first and second measuring portions and for receiving and delivering predetermined volumes of diluent to the isolated precise sample volumes respectively within the first and second measuring portions for delivering the sample volumes and diluent as dilutions to the respective exterior mixing and testing chambers and the rotor being arranged for reverse translation to return the valve assembly to the loading condition subsequent to delivery of the dilutions; the improvement comprising: the valve assembly having an additional measuring portion for measuring and isolating an additional precise sample volume within the valve assembly, said additional measuring portion being in series communication with the first and second measuring portions during the loading condition of the valve assembly, the valve assembly having inert fluid entry means enabling introduction of an inert fluid to said additional measuring portion for the displacement of said additional sample volume to a neutral location displaced from the isolated condition thereof, the valve assembly having lysing reagent inlet means for introducing a predetermined volume of lysing reagent from a source thereof to said displaced additional sample volume at the neutral displaced location thereof to drive both the additional sample volume along with the lysing reagent to an additional mixing and testing chamber exterior to the valve assembly, the valve assembly being free of contamination by the lysing reagent along the interior liquid sample and diluent flow paths therein.

6. The valve assembly according to claim 5 in which the stator has a dedicated through-passageway for receiving the additional sample volume from said additional measuring portion during the delivery condition of the valve assembly, said lysing reagent inlet means being arranged to direct the lysing reagent to said displaced sample volume via said dedicated through-passageway subsequent to return translation of the valve assembly to the loading condition.

7. The valve assembly according to claim 6 in which said neutral location includes a corrosion resistant conduit secured to the stator at said dedicated through-passageway and in communication therewith for receiving the additional sample volume and the lysing reagent.

8. The valve assembly according to claim 7 comprising an inert fluid source including a pressurized air pump for introducing the inert fluid to said inert fluid entry means ends.

9. The valve assembly according to claim 7 in which said lysing reagent is introduced to the additional sample volume simultaneously with introduction of backwash to said additional measuring portion and first and second measuring portions subsequent to return of said valve assembly to the loading condition from the delivery condition.

10. The valve assembly according to any one of claims 5, 6 or 7 in which said additional measuring portion comprises an external loop secured to the rotor, said lyse reagent inlet means comprising an inlet passageway formed in the rotor and said inert fluid entry means comprises an inlet carried by the stator.

11. In a liquid metering and transfer valve assembly for providing at least a pair of isolated precise liquid samples from a single liquid sample source and constructed and arranged for delivering each along with predetermined volumes of diluent to exterior mixing and testing chambers respectively, said valve assembly including at least one stator element, a loading element and a rotor element sandwiched therebetween in aligned frictional sealed face to face engagement, first and second measuring portions carried by the one stator and the rotor respectively, sample inlet means carried by the loading element arranged to establish a continuous series flow path for liquid sample during a loading mode of said valve assembly, the rotor arranged to be translated angularly to an isolating mode during which the flow path is segmented to isolate precise volumes of sample from the flow path, the first measuring portion formed as an axially parallel through-passageway carried by the rotor and the second measuring portion formed as a first external hollow loop secured to the one stator, plural cooperating complementary counterpart passageways formed in the rotor, the stator and the loading element for introducing predetermined volumes of diluent to the first and second measuring portions for delivering the at least a pair of precise volumes of sample and associated diluent as dilutions to the respective exterior mixing and testing chambers and interconnecting the first and second measuring portions; the improvement comprising: means carried by said valve assembly to measure and isolate an additional precise sample volume therewithin, means secured to the rotor for introducing lysing reagent from a source thereof to said additional precise sample volume via the valve assembly without contaminating the interior flow paths for sample and diluent within said valve assembly, the additional sample volume and the lysing agent being deliverable as a mixture from said valve assembly to an additional exterior mixing and testing chamber.

12. The valve assembly according to claim 11 in which said measuring and isolating means comprise a second external hollow loop carried by the rotor and arranged for placement in series communication with the first and second measuring portions during the loading condition of the valve assembly and said means for introducing lysing reagent comprise a lyse reagent inlet passageway carried by the rotor, a dedicated axially parallel through-passageway formed in the one stator and arranged to be disposed in communicating relationship with said second external hollow loop during the delivery condition of the valve assembly, inert fluid entry passageway means formed in one stator and arranged coupled to an inert fluid source, said inert fluid entry passageway means arranged to introduce inert fluid to said second external hollow loop from the inert fluid source for displacing the additional sample volume from said second external hollow loop to a location displaced from the rotor during the delivery condition of said valve assembly, said dedicated passageway arranged to receive the lysing reagent to drive the additional sample volume with the lysing reagent as a mixture to said additional mixing and testing chamber from the displaced location, the rotor being reverse rotatable to return all the first and second measuring portions and measuring and isolating means to a series communicating condition and means directing backwash fluid from a source thereof to the series communicating measuring portions and measuring and isolating means and sample inlet means simultaneously with the driving of said lysing reagent to said additional sample volume.

13. The valve assembly according to claim 12 in which said inert fluid source is arranged to direct an additional pulse of inert fluid to said inert fluid entry passageway means just prior to reverse translation of the rotor to place said valve assembly in the loading condition.

14. In a liquid metering and transfer valve assembly for providing at least a pair of isolated precise liquid sample aliquots from a single liquid sample source and delivering the at least a pair of aliquots to respective exterior locations, the assembly including a stator and a rotor arranged axially aligned in face to face frictional sealed engagement, the rotor being angularly translatable between a loading condition of the valve assembly and a delivery condition of the valve assembly, the rotor carrying at least first and second measuring portions, the stator carrying respective cooperating counterpart passageways, said at least first and second measuring portions being in series communication during the loading condition and liquid sample inlet means for introducing liquid sample to said at least first and second measuring portions during said loading condition, said rotor being angularly translatable to dispose the valve assembly in the delivery condition isolating the at least a pair of liquid sample aliquots in the at least first and second measuring portions respectively and means for introducing at least a predetermined volume of diluent from a source thereof to the first measuring portion for driving the aliquot therein to a first exterior location along with said predetermined volume of diluent during the delivery condition; the improvement comprising, means for introducing a second liquid to the valve assembly without exposing the interior sample flow paths thereof thereto, the second liquid being of the type which is not intended to be exposed to the sample flow paths and other flow paths therein associated with the liquid sample, said means for introducing a second liquid comprising a first dedicated passageway formed in the stator and first and second dedicated entry passageways formed in the rotor, said second dedicated entry passageway arranged to be placed in communication with said first dedicated passageway during the loading condition, means for introducing a gaseous fluid from a source thereof to said first dedicated entry passageway during the delivery condition for driving the aliquot content of the second measuring portion to a displaced location at least within the first dedicated passageway and isolated from said rotor and means for introducing a second liquid to said second dedicated entry passageway with the return of the rotor to the loading condition for driving the displaced aliquot to a second exterior location, the flow path for the second liquid being independent of any internal flow paths followed by the liquid sample and associated diluent.

15. In a liquid metering and transfer valve assembly having the capability of metering, isolating, transferring and delivering precise volume aliquots of a whole blood sample from a source thereof to mixing and testing chambers of a blood analysis system; the improvement comprising: said valve assembly having a precise volume hollow loop for metering and isolating an additional sample aliquot therewithin, first and second dedicated portions, each displaced from said loop, and a first dedicated passageway, said first dedicated passageway arranged to introduce a first inert fluid from a source thereof to said loop to force said additional sample aliquot from an isolated condition to said first dedicated portion, said first and second dedicated portions defining a flow path for introducing lysing reagent to the first dedicated portion to force said additional sample aliquot from a displaced location, as a lysing reagent/aliquot mixture, to a selected additional mixing and testing chamber exterior to said valve assembly without contaminating any interior flow path of said valve assembly which is traversed by a blood sample and associated diluent therewith within said valve assembly.

* * * * *